United States Patent
Liu et al.

(10) Patent No.: US 11,638,789 B2
(45) Date of Patent: May 2, 2023

(54) SAFE EJECTION INTRAVENOUS NEEDLE

(71) Applicant: JIANGSU KANGBAO MEDICAL EQUIPMENT CO., LTD, Yangzhou (CN)

(72) Inventors: Hui Liu, Yangzhou (CN); Wenbin Fan, Yangzhou (CN)

(73) Assignee: JIANGSU KANGBAO MEDICAL EQUIPMENT CO., LTD, Yangzhou (CN)

( * ) Notice: Subject to any disclaimer, the term of this patent is extended or adjusted under 35 U.S.C. 154(b) by 0 days.

(21) Appl. No.: 17/767,936

(22) PCT Filed: Oct. 21, 2019

(86) PCT No.: PCT/CN2019/112210
§ 371 (c)(1),
(2) Date: May 25, 2022

(87) PCT Pub. No.: WO2021/068280
PCT Pub. Date: Apr. 15, 2021

(65) Prior Publication Data
US 2023/0090581 A1  Mar. 23, 2023

(30) Foreign Application Priority Data

Oct. 11, 2019  (CN) .......................... 201910963151.X

(51) Int. Cl.
*A61M 5/32* (2006.01)
*A61M 5/34* (2006.01)

(52) U.S. Cl.
CPC .......... *A61M 5/3257* (2013.01); *A61M 5/348* (2013.01)

(58) Field of Classification Search
CPC .. A61M 5/3202; A61M 5/3205; A61M 5/321; A61M 5/3243; A61M 5/3245;
(Continued)

(56) References Cited

U.S. PATENT DOCUMENTS

| 4,923,447 A | * | 5/1990 | Morgan | .............. A61M 5/3271 604/263 |
| 5,201,708 A | * | 4/1993 | Martin | ................ A61M 5/3271 604/110 |

(Continued)

FOREIGN PATENT DOCUMENTS

| CN | 201759929 U | 3/2011 |
| CN | 105561433 A | 5/2016 |

(Continued)

*Primary Examiner* — Kami A Bosworth
(74) *Attorney, Agent, or Firm* — Bayramoglu Law Offices LLC

(57) ABSTRACT

An ejection-type safety intravenous needle includes a sheath, a hub, a cannula fixed on the hub, and a base. An accommodation cavity is formed in the base. The hub is fixed in the accommodation cavity, and the cannula is exposed outside of the accommodation cavity. The sheath encloses the cannula, and a bottom of the sheath is located in the accommodation cavity and provided with a first limiting structure. A second limiting structure cooperating with the first limiting structure is provided at a top of the accommodation cavity. An elastic element is provided in the accommodation cavity, and the elastic element abuts against a bottom end of the sheath. A top and a bottom of the base are provided with a first clamping structure and a second clamping structure, respectively. A third clamping structure cooperating with the first clamping structure and the second clamping structure is provided on the sheath.

9 Claims, 5 Drawing Sheets

(58) Field of Classification Search
CPC .............. A61M 5/3257; A61M 5/3269; A61M 5/3271; A61M 5/3272; A61M 2005/1587; A61M 2005/3247; A61M 2005/3252; A61M 2005/3258; A61M 25/0612; A61M 25/0618; A61M 25/0625; A61M 25/0631; A61M 25/0637

See application file for complete search history.

(56) References Cited

U.S. PATENT DOCUMENTS

| | | | |
|---|---|---|---|
| 5,472,430 | A | 12/1995 | Vaillancourt |
| 2002/0103464 | A1 | 8/2002 | Crawford et al. |
| 2003/0120222 | A1 | 6/2003 | Vaillancourt |
| 2005/0267416 | A1* | 12/2005 | Mohammed ........ A61M 5/3272 128/919 |
| 2006/0271001 | A1* | 11/2006 | Hirota ................... A61M 5/158 604/177 |
| 2007/0060840 | A1* | 3/2007 | Conway ........... A61B 5/150633 604/164.08 |

FOREIGN PATENT DOCUMENTS

| | | |
|---|---|---|
| CN | 106237454 A | 12/2016 |
| CN | 106540354 A | 3/2017 |
| CN | 107754048 A | 3/2018 |

\* cited by examiner

SAFE EJECTION INTRAVENOUS NEEDLE

CROSS REFERENCE TO THE RELATED APPLICATIONS

This application is the national phase entry of International Application No. PCT/CN2019/112210, filed on Oct. 21, 2019, which is based upon and claims priority to Chinese Patent Application No. 201910963151.X, filed on Oct. 11, 2019, the entire contents of which are incorporated herein by reference.

TECHNICAL FIELD

The present disclosure belongs to the technical field of medical instruments, and in particular to an ejection-type safety intravenous needle.

BACKGROUND

As a common medical instrument, the intravenous needle is mainly used for intravenous fluid transfusion, blood transfusion or blood sampling in a clinic. An existing intravenous needle is mainly composed of a cannula, a hub and a sheath. For ease of operation, a paddle is further provided at a bottom of the hub, the cannula is fixed on the hub, and the sheath is sleeved on the hub. With such a structure in which the sheath is just sleeved on the cannula, if the sheath is made of rubber and other materials having a large frictional force, the sheath is easily pierced by a tip to injure the operator despite the firmer connection with the cannula. Hence, the sheath is usually made of a hard material. In this case, there is a big gap between the sheath and the cannula to cause a poor connection, such that the operator is liable to knock off the sheath accidentally and get injured during use of the intravenous needle.

SUMMARY

The present disclosure provides an ejection-type safety intravenous needle to solve the above technical problem in the art.

In order to achieve the above objective, the present disclosure employ the following technical solutions:

An ejection-type safety intravenous needle includes a sheath, a hub, and a cannula fixed on the hub, and further includes a base, where an accommodation cavity is formed in the base; the hub is fixed in the accommodation cavity, and the cannula is exposed outside of the accommodation cavity; the sheath encloses the cannula, and a bottom of the sheath is located in the accommodation cavity and provided with a first limiting structure; a second limiting structure cooperating with the first limiting structure is provided at a top of the accommodation cavity; an elastic element is provided in the accommodation cavity, and the elastic element abuts against a bottom end of the sheath; a top of the base is provided with a first clamping structure, and a bottom of the base is provided with a second clamping structure; a third clamping structure cooperating with the first clamping structure and the second clamping structure is provided on the sheath; the first clamping structure is connected to the third clamping structure in an initial state; under the action of a first external force, the first clamping structure can be separated from the third clamping structure; in a state in which the first clamping structure is separated from the second clamping structure, and under the action of a second external force, the sheath can slide toward the elastic element until the second clamping structure is connected to the third clamping structure, such that the cannula is exposed outside of the sheath; and the first external force and the second external force are in different directions.

Before the ejection-type safety intravenous needle provided by the present disclosure is used, the sheath encloses the cannula to prevent a sharp tip of the cannula from injuring people. The elastic element abuts against the bottom end of the sheath to prevent easy withdrawal of the sheath. As the first limiting mechanism cooperates with the second limiting mechanism, the sheath is not knocked off and separated from the base. As the first clamping structure cooperates with the third clamping structure, the sheath is not stressed for withdrawal to expose the tip of the cannula. The first external force and the second external force are in the different directions, so the sheath does not move even though accidentally knocked by the people.

When the ejection-type safety intravenous needle is used, the first external force is applied to the third clamping structure, such that the first clamping structure is separated from the third clamping structure. Thereafter, the second external force is applied, which ensures that the sheath slides toward the elastic element until the second clamping structure is connected to the third clamping structure, such that the cannula is exposed outside of the sheath. In this case, the elastic element stores energy. As the second clamping structure is connected to the third clamping structure, the sheath is prevented from moving upward and thus the medical staff can use the product normally.

As a preferable implementation, under the action of a third external force, the second clamping structure may be separated from the third clamping structure, and the sheath may be restored to the initial state under the action of the elastic element, where the third external force and a force of the elastic element acting on the sheath are in different directions. With such a structure, the ejection-type safety intravenous needle used can be restored to the initial state, and thus can prevent the tip of the cannula from being exposed outside of the sheath to injure people before and after use. As the third external force and the acting force of the elastic element to the sheath are in the different directions, the sheath is not bounced accidentally to affect the use.

As a preferable implementation, the first limiting structure may be a non-return piece, and the second limiting structure may be a non-return limiting ring. With such a structure, the sheath is fixed more firmly.

As a preferable implementation, a lower sliding slot may be formed in a side of the base in a penetrating manner; a lower locking slot may be formed in a bottom of the lower sliding slot; the lower locking slot may form the second clamping structure; a paddle may be provided at the top of the base; an upper locking slot may be formed in a top of the paddle; an upper sliding slot may be formed below the upper locking slot in a penetrating manner; the upper sliding slot may communicate with the lower sliding slot; the upper sliding slot and the upper locking slot may form the first clamping structure; a snap lock may be provided on the sheath; a top of the snap lock may be provided with an upper locking hook cooperating with the upper locking slot, and a bottom of the snap lock may be provided with a lower locking hook cooperating with the lower locking slot; the upper locking hook may be downward, and the lower locking hook may be upward; and the upper locking hook and the lower locking hook may form the third clamping structure. The structure is simple, and the use is convenient.

As a preferable implementation, a connecting seat may be provided on the snap lock and located between the upper locking hook and the lower locking hook; the connecting seat may be connected to the sheath; and the connecting seat may be slidably connected to a through sliding slot formed by the upper sliding slot and the lower sliding slot. The connecting seat is more convenient for the operation of the medical staff.

Specifically, each of the upper locking hook and the lower locking hook may be formed with an angle of 10-70°.

Specifically, the elastic element may be a spring, and the spring may be sleeved on the hub.

An end of the hub without being connected to the cannula may penetrate through the base, for ease of connection with a catheter.

Preferably, the end of the hub without being connected to the cannula may be connected to a catheter, for ease of the use.

Preferably, the base may be of a cylindrical shape, to adapt to the use of the product.

In the figure: 1. sheath, 11. snap lock, 111. top of the snap lock, 112. bottom of the snap lock, 113. connecting seat, 12. upper locking hook, 13. lower locking hook, 14. non-return piece, 2. paddle, 21. upper locking slot, 22. upper sliding slot, 3. hub, 31. lower locking slot, 32. lower sliding slot, 33. cannula, 34. non-return limiting ring, 35. base, 4. spring, and 5. catheter.

DETAILED DESCRIPTION OF THE EMBODIMENTS

To make the objectives, technical solutions, and advantages of the present disclosure clearer, the present disclosure is further described below with reference to the accompanying drawings and specific embodiments. It should be understood that the specific embodiments described herein are merely intended to explain the present disclosure, rather than to limit the present disclosure. All other embodiments obtained by those of ordinary skill in the art based on the embodiments of the present disclosure without creative efforts shall fall within the protection scope of the present disclosure.

Figure 1:
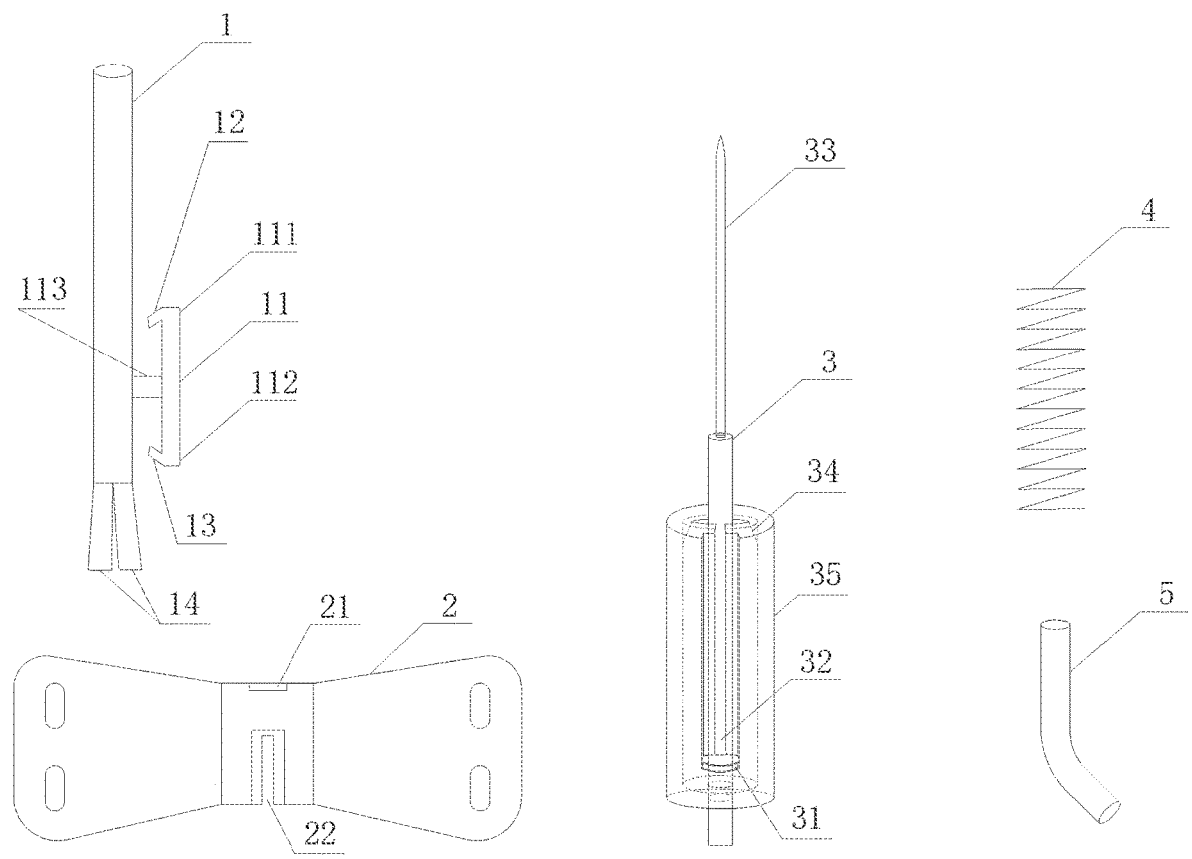
FIG. 1 is a schematic view illustrating a breakdown structure of an ejection-type safety intravenous needle according to the present disclosure.
Figure 2:
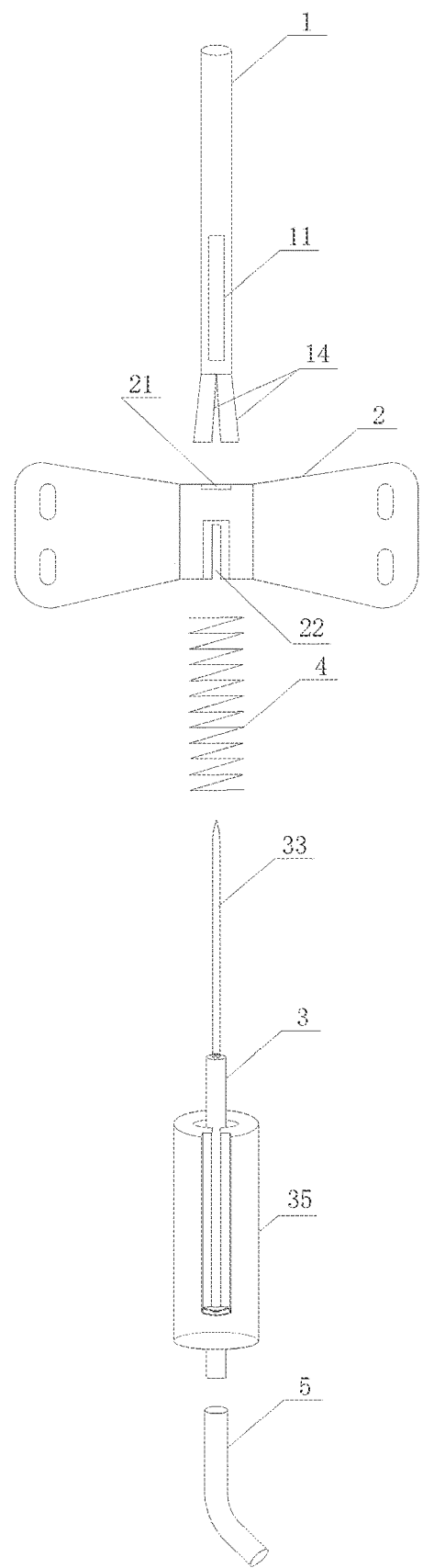
FIG. 2 is a schematic view illustrating an exploded structure of an ejection-type safety intravenous needle according to the present disclosure.

The present disclosure provides an ejection-type safety intravenous needle. Referring to FIG. 1 and FIG. 2, the ejection-type safety intravenous needle includes a sheath 1, a hub 3, and a cannula 33 fixed on the hub, and further includes a base 35. An accommodation cavity is formed in the base. The base may usually be of a cylindrical shape, and the corresponding accommodation cavity may also be of a cylindrical shape. The hub is fixed in the accommodation cavity, and the cannula is exposed outside of the accommodation cavity. The sheath encloses the cannula, and a bottom of the sheath is located in the accommodation cavity and provided with a non-return piece 14. A non-return limiting ring 34 cooperating with the non-return piece is provided at a top of the accommodation cavity. The non-return limiting ring is usually a truncated-cone-shaped ring and is integrally formed with the base. A spring 4 is provided in the accommodation cavity. The spring is sleeved on the hub, and abuts against a bottom end of the sheath. A lower sliding slot 32 is formed in a side of the base in a penetrating manner. A lower locking slot 31 is formed in a bottom of the lower sliding slot 32. The lower locking slot forms a second clamping structure. A paddle 2 is provided at a top of the base. An upper locking slot 21 is formed in a top of the paddle. An upper sliding slot 22 is formed below the upper locking slot in a penetrating manner. The upper sliding slot communicates with the lower sliding slot. The upper sliding slot and the upper locking slot form a first clamping structure. The paddle may further be integrally provided with a cylinder, for ease of connection with the cylindrical base. A snap lock 11 is provided on the sheath. A top of the snap lock 11 is provided with an upper locking hook 12 cooperating with the upper locking slot, and a bottom of the snap lock 11 is provided with a lower locking hook 13 cooperating with the lower locking slot. The upper locking hook is downward, and the lower locking hook is upward. The upper locking hook and the lower locking hook form a third clamping structure. A connecting seat 113 is provided on the snap lock and located between the upper locking hook and the lower locking hook. The connecting seat is connected to the sheath. The connecting seat, the sheath and the snap lock are often integrally formed. The connecting seat is slidably connected to a through sliding slot formed by the upper sliding slot 22 and the lower sliding slot 32.

Figure 3:
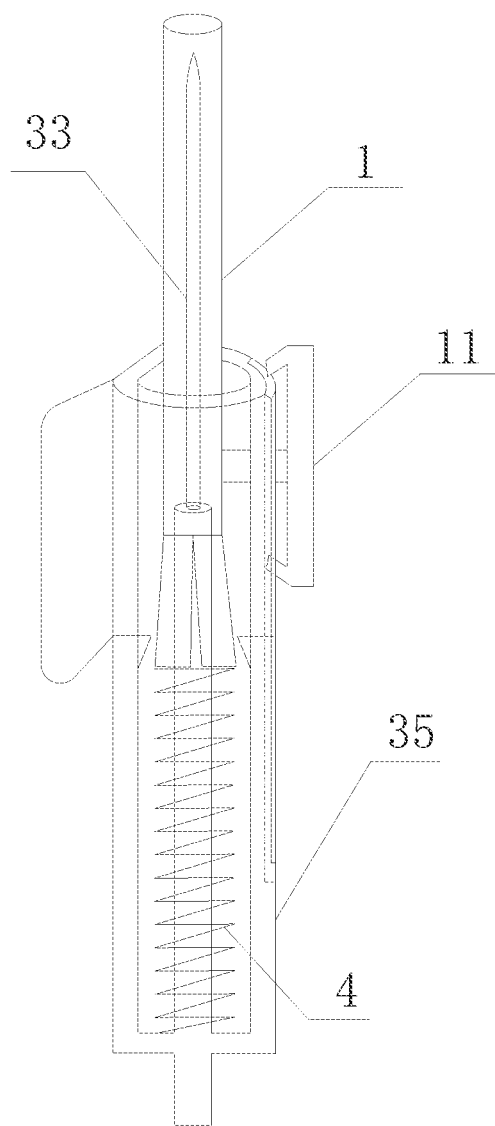
FIG. 3 is a schematic view illustrating an initial state of an ejection-type safety intravenous needle according to the present disclosure.

Components of the ejection-type safety intravenous needle have the following structures and functions in use:

The state of the product from the factory is as shown in FIG. 3. The cannula 33 is protected by the sheath 1, which prevents a sharp tip of the cannula from injuring people. The spring 4 is not compressed, with upper and lower ends abutting against the non-return piece 14 and the bottom of the base 35. The upper locking hook 12 at the top of the snap lock 11 is firmly locked in the upper locking slot 21 at the top of the paddle 2, which prevents the sheath 1 from sliding freely and the sharp tip exposed outside of the cannula 33 due to false touch from injuring people.

Figure 4:
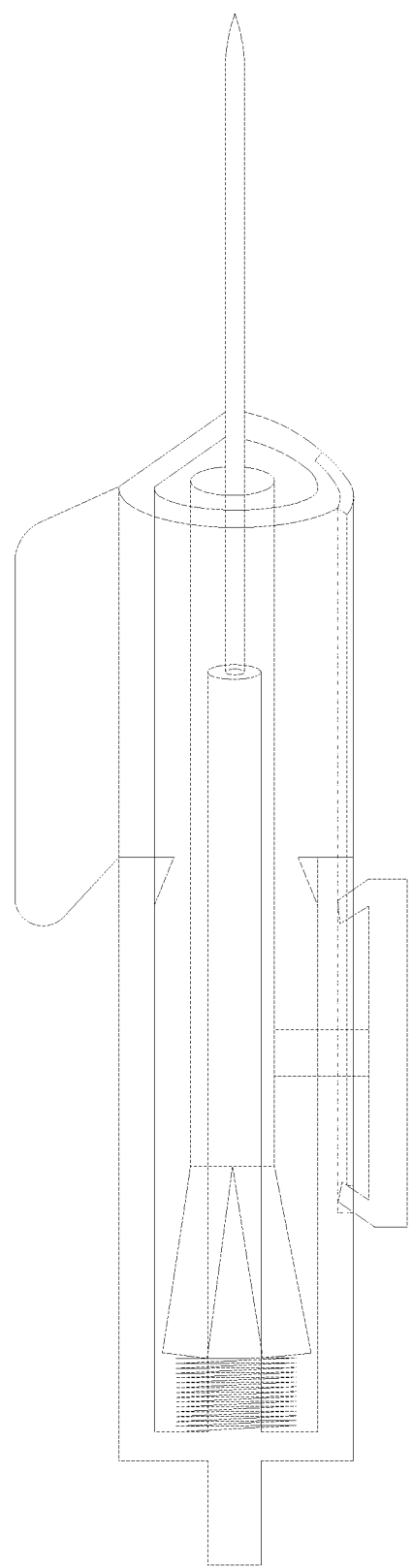
FIG. 4 is a schematic view illustrating a use state of an ejection-type safety intravenous needle according to the present disclosure.

When the ejection-type safety intravenous needle is used, the medical staff takes it out from an aseptic package, with a finger gently pressing a bottom 112 of the snap lock 11. As a result, the upper locking hook 12 is separated from the upper locking slot 21 where the intravenous needle from the factory is locked, the connecting seat 113 on the sheath 1 under the action of an external force can slide downward along a through and smooth sliding slot formed by the upper sliding slot 22 and the lower sliding slot 32 to the bottom of the sliding slot, and the lower locking hook 13 hooks the lower locking slot 31 to enter a safety state of the sheath, as shown in FIG. 4. Thus, the ejection-type safety intravenous needle is prepared well for a blood vessel puncture, and can be used by the medical staff for corresponding therapeutic applications.

Figure 5:
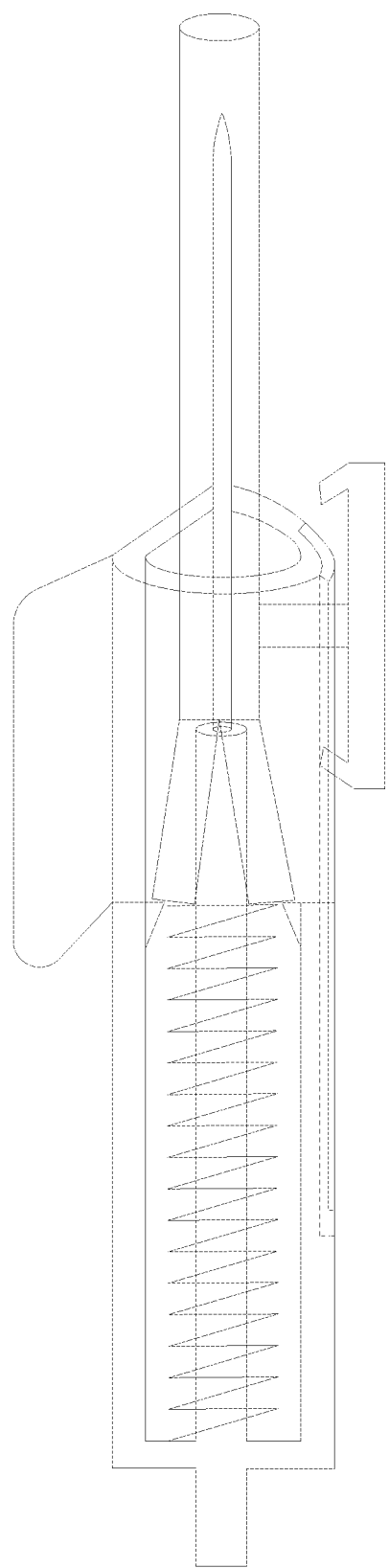
FIG. 5 is a schematic view illustrating a restored state of an ejection-type safety intravenous needle according to the present disclosure.

The intravenous needle used by the medical staff can be abandoned. In this case, the bottom 112 of the snap lock 11 is pressed gently and pulled back slightly, such that the lower locking hook 13 is separated from the lower locking slot 31 to terminate the safety state of the sheath. The finger releases the bottom 112 of the snap lock 11. Under the action of an elastic force of the spring 4, the sheath 1 is ejected upward along the through and smooth sliding slot formed by the upper sliding slot 22 and the lower sliding slot 32. With the inertia of the ejection, the non-return piece 14 passes through the non-return limiting ring 34, the sheath 1 is limited firmly above a top opening end of the base 35, and thus the sheath 1 encloses the sharp tip of the cannula 33 completely, as shown in FIG. 5. Therefore, there is no secondary injury to people. The lower locking hook 13 can also be separated from the lower locking slot 31 by directly pressing the top 111 of the snap lock 11. Usually, each of the upper locking hook and the lower locking hook is formed with an angle of 10-70°.

It is to be noted that the above solution is merely a preferred technical solution. The non-return piece and the non-return limiting ring may also be replaced by other limiting structures, provided that the limiting function can be realized. The spring may also be an existing elastic element such as a shrapnel, which is known to those skilled in the art and is not repeated herein. The first clamping structure, the second clamping structure and the third clamping structure may also be other clamping structures. An end of the hub without being connected to the cannula penetrates through the base, for ease of connection with a catheter. Certainly, the end of the hub without being connected to the cannula may also be directly connected to a catheter 5. The catheter may further be connected to a luer fitting for ease of the use.

The above embodiments are merely illustrative of some implementations of the present disclosure, and the description thereof is specific and detailed, but should not be construed as limiting the patent scope of the present disclosure. It should be noted that those of ordinary skill in the art can further make several variations and improvements without departing from the idea of the present disclosure, but such variations and improvements shall all fall within the protection scope of the present disclosure. Therefore, the protection scope of the present disclosure shall be subject to the appended claims.

What is claimed is:

1. An ejection-type safety intravenous needle, comprising a sheath, a hub, a cannula fixed on the hub, and a base, wherein an accommodation cavity is formed in the base;
   the hub is fixed in the accommodation cavity, and the cannula is exposed outside of the accommodation cavity;
   the sheath encloses the cannula, and a bottom of the sheath is located in the accommodation cavity and provided with a first limiting structure;
   a second limiting structure configured to cooperate with the first limiting structure is provided at a top of the accommodation cavity;
   an elastic element is provided in the accommodation cavity, and the elastic element abuts against a bottom end of the sheath;
   a top of the base is provided with a first clamping structure, and a bottom of the base is provided with a second clamping structure;
   a third clamping structure configured to cooperate with the first clamping structure and the second clamping structure is provided on the sheath;
   the first clamping structure is configured to be connected to the third clamping structure in an initial state;
   wherein, when under an action of a first external force, the first clamping structure is separated from the third clamping structure;
   wherein, when in a state in which the first clamping structure is separated from the third clamping structure, and when under an action of a second external force, the sheath is configured to slide toward the elastic element until the second clamping structure is connected to the third clamping structure, such that the cannula is exposed outside of the sheath; and
   the first external force and the second external force are in different directions;
   wherein a lower sliding slot is formed in a side of the base in a penetrating manner, a lower locking slot is formed in a bottom of the lower sliding slot, and the lower locking slot forms the second clamping structure;
   a paddle is provided at the top of the base;
   an upper locking slot is formed in a top of the paddle;
   an upper sliding slot is formed below the upper locking slot in a penetrating manner;
   the upper sliding slot communicates with the lower sliding slot;
   the upper sliding slot and the upper locking slot form the first clamping structure;
   a snap lock is provided on the sheath;
   a top of the snap lock is provided with an upper locking hook to cooperate with the upper locking slot, and a bottom of the snap lock is provided with a lower locking hook to cooperate with the lower locking slot;
   the upper locking hook is downward, and the lower locking hook is upward; and
   the upper locking hook and the lower locking hook form the third clamping structure.

2. The ejection-type safety intravenous needle according to claim 1, wherein when under an action of a third external force, the second clamping structure is configured to be separated from the third clamping structure, and the sheath is configured to be restored to the initial state when under an action of the elastic element, wherein the third external force and a force of the elastic element are configured to act on the sheath in different directions.

3. The ejection-type safety intravenous needle according to claim 1, wherein the first limiting structure is a non-return piece, and the second limiting structure is a non-return limiting ring.

4. The ejection-type safety intravenous needle according to claim 1, wherein a connecting seat is provided on the snap lock and located between the upper locking hook and the lower locking hook, and the connecting seat is connected to the sheath; and
   the connecting seat is slidably connected to a through sliding slot formed by the upper sliding slot and the lower sliding slot.

5. The ejection-type safety intravenous needle according to claim 4, wherein each of the upper locking hook and the lower locking hook is formed with an angle of 10-70°.

6. The ejection-type safety intravenous needle according to claim 1, wherein the elastic element is a spring, and the spring is sleeved on the hub.

7. The ejection-type safety intravenous needle according to claim 6, wherein an end of the hub opposite the cannula is connected to a catheter.

8. The ejection-type safety intravenous needle according to claim 1, wherein an end of the hub opposite the cannula penetrates through the base.

9. The ejection-type safety intravenous needle according to claim 1, wherein the base is of a cylindrical shape.

* * * * *